United States Patent
Gevers et al.

(10) Patent No.: US 8,829,240 B2
(45) Date of Patent: Sep. 9, 2014

(54) PROCESS FOR THE PRODUCTION OF UREA FROM AMMONIA AND CARBON DIOXIDE

(75) Inventors: Lambertus Wilhelmus Gevers, Munstergeleen (NL); Jozef Hubert Meessen, Wijlre (NL); Johannes Henricus Mennen, Meijel (NL)

(73) Assignee: Stamicarbon B.V., Sittard (NL)

( * ) Notice: Subject to any disclaimer, the term of this patent is extended or adjusted under 35 U.S.C. 154(b) by 648 days.

(21) Appl. No.: 12/992,890

(22) PCT Filed: May 19, 2009

(86) PCT No.: PCT/EP2009/056066
§ 371 (c)(1),
(2), (4) Date: Feb. 3, 2011

(87) PCT Pub. No.: WO2009/141344
PCT Pub. Date: Nov. 26, 2009

(65) Prior Publication Data
US 2011/0118506 A1  May 19, 2011

(30) Foreign Application Priority Data
May 19, 2008  (EP) ................................. 08156422

(51) Int. Cl.
*C07C 273/00*  (2006.01)
*C07C 273/04*  (2006.01)

(52) U.S. Cl.
CPC ................................. *C07C 273/04* (2013.01)
USPC .......................................................... 564/67

(58) Field of Classification Search
CPC ..................... C07C 273/04; B01J 2219/00076
USPC .......................................................... 564/67
See application file for complete search history.

(56) References Cited

U.S. PATENT DOCUMENTS 2,727,069 A   12/1955  Van Waes
3,406,201 A * 10/1968  Baumann et al. ............... 564/70

FOREIGN PATENT DOCUMENTS

EP   0 329 215        8/1989
EP     329215 A1 *   8/1989
GB   1 188 051        4/1970

OTHER PUBLICATIONS

Blawert et al., Surface Coatings Technology, 85 (1996) 15-27.*
Duplex Steel Outokumpu Technical Manual (http://www.outokumpu.com/en/Products/strip/grades/Duplex-Austenitic-Ferritic/Pages/default.aspx).*
Office Action issued for Chinese Patent Application No. 200980128356.0 dated Dec. 5, 2012, 12 pages (including English translation).
International Search Report for EP/2009/056066, mailed on Jul. 29, 2009, 2 pages.

* cited by examiner

Primary Examiner — Sudhakar Katakam
Assistant Examiner — Kofi Adzamli
(74) Attorney, Agent, or Firm — Morrison & Foerster LLP

(57) ABSTRACT

Process for the production of urea from ammonia and carbon dioxide in a urea plant containing a high-pressure synthesis section comprising at least one reactor section, a stripper and a condenser wherein all the high-pressure equipment is placed in a low position, wherein the height of the high-pressure section is less than 35 m from ground level and at least one of the reactor sections comprises means for the separate distribution of ammonia in the bottom of the reactor section.

18 Claims, 1 Drawing Sheet

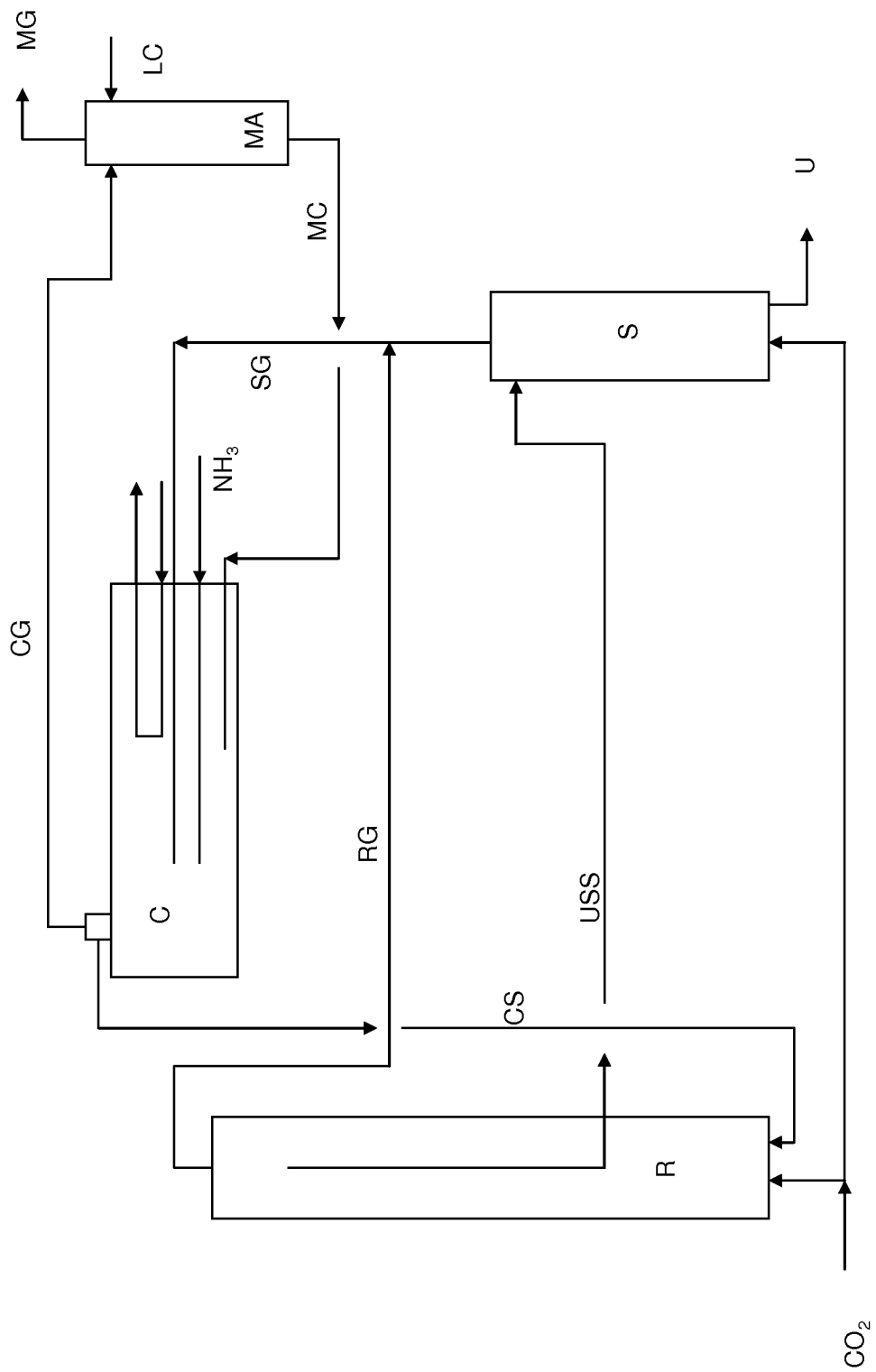

PROCESS FOR THE PRODUCTION OF UREA FROM AMMONIA AND CARBON DIOXIDE

CROSS-REFERENCE TO RELATED APPLICATIONS

This application is the national phase of PCT application PCT/EP2009/056066 having an international filing date of 19 May 2009, which claims benefit of European application No. 08156422.1 filed 19 May 2008. The contents of the above patent applications are incorporated by reference herein in their entirety.

The invention is directed to a process for the production of urea from ammonia and carbon dioxide in a urea plant containing a high-pressure synthesis section comprising at least one reactor section, a stripper and a condenser wherein all the high-pressure equipment is placed in a low position.

Stripping processes for the production of urea wherein all high-pressure equipment is placed on ground level are known in the art. An example of such a process is described in GB-1188051. In this patent publication is described that such a process can be obtained by using an ejector in the main recycle flow in the high-pressure part of the equipment. In the process described according to GB-1188051 a process with all equipment on ground level can be achieved by using an ammonia-driven ejector for the transport of a carbamate stream from the condenser to the reactor.

A disadvantage of the use of an ejector in the main recycle flow is that all ammonia is needed as driving fluid in the ejector and can thus not be supplied at other places in the high-pressure synthesis section. Moreover, in the discharge of the ejector a combined stream of ammonia and carbamate will always be obtained. For the reasons mentioned above the urea process is not flexible and no easy adaptation of process conditions is possible.

Another disadvantage of the use of an ejector is an increase of energy consumption. The ammonia used as driving agent in the ejector has to be supplied to the motive fluid inlet of the ejector at a pressure substantially above the main synthesis pressure. This implies that the energy consumption of the pump that is used to supply the ammonia to the urea synthesis section has to be increased considerably.

The object of the invention is to overcome these disadvantages.

The invention is characterized in that the height of the high-pressure section is less than 35 m from ground level and at least one of the reactor sections comprises means for the separate distribution of ammonia over the volume of the reactor section.

Preferably, the height of the high-pressure section is less than 30 m from ground level.

This has the advantage that a better distribution of ammonia in the reactor section can be obtained and therefore a better conversion to urea in the reactor section is possible. This has the result that in a smaller reactor section the same amount of conversion can be obtained, so that a reactor section with a smaller volume is sufficient. Smaller equipment is cheaper and thus the process for the production of urea can be built more cost efficiently.

Alternatively, the advantage of a better distribution of ammonia in the reaction section could be used to obtain a better conversion in the same volume. In such a case, the amount of non-converted carbamate is reduced, such that the energy used by the equipment involved in the recycle of this non-converted material is reduced.

A combination of these two advantages is also possible, resulting in reduction of cost, as well as reduction in energy consumption.

According to the invention ammonia is distributed in an optimized way over at least one reactor section of the high-pressure synthesis section. Optimized in this context means that ammonia is supplied at multiple locations over the volume of at least one reactor section in the urea production process. Such distribution of ammonia in practice can be achieved by many provisions. A very cost effective way of doing this is by means of a so called sparger, that consists out of one or more pipes or pipe sections, containing holes for the outflow of ammonia along these pipes. By choosing the diameter and location of these outflow holes, the distribution of ammonia over the volume of the reactor section can be optimized, either towards minimum volume, or towards maximum conversion, or towards a combination of minimum volume and maximum conversion.

In the process according to the invention preferably the flow of the synthesis solution from the reactor section to the stripper, the flow of the mixed gas stream from the stripper to the condenser and of the condensate from the condenser to the reactor section is a gravity flow. This means that no ejector, compressor or pump is present for rising the fluid pressure in the main recycle flow in the high-pressure section. For this reason the complete amount of ammonia that is fed to the high-pressure synthesis section is available for purposive distribution via a sparger to the reactor section.

A process for the production of urea contains a high-pressure synthesis section and one or more recovery sections at lower pressure. The high-pressure section comprises a reactor section in which the urea synthesis solution is prepared, a stripper in which the urea synthesis solution is stripped and a condenser in which the gases released in the stripping zone are condensed.

The synthesis can be carried out in more than one reactor section. A reactor section is herewith defined as a section wherein at least 20 wt % of the total amount of urea in the synthesis section is formed.

The reactor sections can be placed in serial order or parallel and can be two separate vessels or two reactor sections placed in one vessel. A reactor section can also be combined with a condenser section in one vessel. When the condenser is a submerged condenser and the residence time in the condenser section is long enough, more than 20 wt % of the total amount of urea is formed in the condenser and it thus functions as a reactor section.

Ammonia and carbon dioxide are fed to the reactor section either directly or indirectly. Ammonia and carbon dioxide can be introduced to the process for the production of urea at various places in the high-pressure synthesis section or in the recovery sections.

Preferably, carbon dioxide is mainly used as a counter-current gas stream during stripping of the urea synthesis solution. A part of the carbon dioxide can be fed to the reactor section.

Preferably, ammonia is fed to the condenser.

In the stripper the urea synthesis solution is stripped counter-current with carbon dioxide with the supply of heat. It is also possible to use thermal stripping. Thermal stripping means that ammonium carbamate in the urea synthesis solution is decomposed and the ammonia and carbon dioxide present are removed from the urea solution exclusively by means of the supply of heat. Stripping may also be effected in two or more steps. The gas stream containing ammonia and carbon dioxide that is released from the stripper is sent to a high-pressure condenser. The gas mixture obtained in the stripper is condensed under the removal of heat and absorbed in the high-pressure condenser, following which the resulting ammonium carbamate is transferred to the reactor section for the formation of urea.

The high-pressure condenser can for example be a falling-film condenser or a so-called submerged condenser as described in NL-A-8400839. The submerged condenser can be placed horizontally or vertically.

Several combinations of condenser sections and reaction sections are possible according to the invention:

Combination of a condenser section with a reaction section in so called submerged or poolcondensers. The submerged or poolcondenser is preferably placed horizontally.

Combination of the condenser with a reaction section into a single vessel, called poolreactor.

In case such a combination of the condenser with a reaction section is applied, it is of particular importance to obtain an optimized distribution of the liquid ammonia in the condenser using means for the distribution of ammonia, since the composition of the content of the condenser changes considerably along the condensation path, because urea formation takes place together with the condensation of the mixed gas coming from the stripper. This formation of urea, and thus also water, along the condensation path results in a change of the optimal $NH_3/CO_2$ ratio along the condensation path. Optimal here is defined as the ratio resulting in the highest possible temperature, which is desirable to increase the reaction speed, as well as to maximize the available temperature difference for heat-exchange. In this way, optimizing the $NH_3/CO_2$ ratio along the condensation path both reduces the required area for heat transfer, as well as reduces the required condensation volume for the ammonium carbamate dehydration reaction.

As the condenser is a submerged condenser and the residence time in the condenser section is long enough, more than 20 wt % of the total amount of urea is formed in the condenser and it thus functions as a reaction section.

Thus, preferably the reactor section comprising the means for distribution of ammonia is a submerged condenser that is, more preferably, placed horizontally.

In cases where the condenser and the first and second part of the reaction section are combined in one vessel, it may even be advantageous to extend the means for distribution of ammonia into the reaction section. In this way also in the reaction section the $NH_3/CO_2$ ratio along the reaction path can be optimized, whereby higher temperatures and consequently a smaller reaction volume are obtained in the reaction section.

Preferably, the reactor section according to the invention is a horizontally placed combination of a submerged condenser and a reactor section, wherein the means for distribution of ammonia is placed in the condensation section and extends, more preferably, into the reaction section.

In the high-pressure synthesis section the pressure is substantially equal to the urea synthesis pressure in the reactor sections, which is the pressure at which urea formation takes place. The urea synthesis pressure is usually a pressure between 11-40 MPa, preferably 12.5-19 MPa. The pressure in the rest of the high-pressure section is substantially equal to the pressure in the reactor section. Substantially equal means that the pressure in the rest of the high-pressure section is less than 0.5 MPa higher or lower than in the reactor section.

In a preferred embodiment of the present invention, the stripper as well as the second reaction section are located on ground level in the plant. In this way, two heavy pieces of equipment are located at a very low elevation in the plant, which results in a considerable reduction of the required investment costs of the structure that has to carry these heavy pieces of equipment. The low location of these pieces of equipment further simplifies the operation and maintenance activities that are required on these equipment items. Also, from a safety point of view, low elevation of heavy pieces of equipment is preferred, since it minimizes the activities of human beings at high level and optimizes safety during construction and operation of the plant.

An oxidizing agent is added to the process for the production of urea in order to protect the materials of construction against corrosion. An oxide skin is formed on the metal parts, which protects against corrosion. This process is known as passivation. The passivating agent may be oxygen or an oxygen-releasing compound as described in for example U.S. Pat. No. 2,727,069. Oxygen can be added, for instance, in the form of air or as a peroxide.

The corrosion sensitive parts in the high-pressure section in the process for the production of urea can be made of a an austenitic-ferritic duplex steel with a chromium content of between 26 and 35 wt. % and a nickel content of between 3 and 10 wt %. This type of steel is less corrosion sensitive. When this type of steel is used for the construction of the reactor section and the stripper it is possible to reduce or omit the introduction of an oxidizing agent to the process for the production of urea. Preferably, the chromium content of the austenitic-ferritic duplex steel is between 26-30 wt %. In the high-pressure section preferably the reactor section and the stripper are made of the austenitic-ferritic duplex steel.

In the recovery section ammonia and carbon dioxide that were not removed from the urea synthesis solution in the stripper are recovered from the urea-comprising stream, produced in the high-pressure synthesis section, in order to be recycled to the high-pressure section. In the recovery section the pressure is lower than in the high-pressure synthesis section. In the process for the production of urea according to the present invention at least one low-pressure recovery section is present. When more than one recovery section is present at least one of the recovery sections is operated at medium pressure and one at low pressure.

Medium pressure is a pressure between 1.0 and 8.0 MPa, preferably between 1.2 and 3.0 MPa. Low pressure is a pressure between 0.2 and 0.8 MPa, preferably between 0.3 and 0.5 MPa.

The synthesis gas that has not reacted in the reactor section can be removed from the reactor section and can be sent to a scrubber, wherein ammonia and carbon dioxide present in the gas flow are removed from the gas flow by absorption in a low-pressure carbamate stream. This carbamate stream is recycled from the low-pressure recovery section of the process for the production of urea. The scrubber can be operated at high-pressure or at medium-pressure. Preferably a medium-pressure scrubber is applied, because a medium-pressure apparatus is cheaper to construct. The scrubbing process in the scrubber can be stimulated by using a heat exchanger that extracts heat from the process. The carbamate stream from the medium-pressure or high-pressure scrubber can be returned to the reactor section, optionally via the high-pressure carbamate condenser.

The invention will hereafter be explained in more detail in the examples without being limited thereto.

EXAMPLE 1

An example of a process according to the invention is given in FIG. 1. The high-pressure part of the process for the production of urea according to FIG. 1 comprised a reactor section (R), a $CO_2$ stripper (S) and a submerged condenser/reactor section (C) that was placed horizontally. Further the process comprised a medium-pressure absorber (MA) and a low-pressure recovery section where the urea stream (U) was further purified.

A small amount of carbon dioxide was fed to the reactor section (R). In the reactor section a urea synthesis solution (USS) was formed which was sent to stripper (S) and stripped by the addition of heat and with carbon dioxide as a stripping gas. During stripping a mixed gas stream (SG) was obtained that was, together with reaction gases (RG) coming from the top of the reactor section (R) fed, via a sparger, to the condenser/reactor section. To the condenser/reactor section also a carbamate stream (MC) coming from the medium-pressure absorber (MA) was fed via a separate sparger. Also fresh ammonia was fed to the condenser/reactor section (C) via a separate sparger. The sparger for the distribution of ammonia and the sparger for distribution of the mixed gas (SG) were placed in the condenser section, but also extended into the reactor section of submerged condenser/reactor (C). The urea solution (CS) formed was sent to the reactor section (R) and the gases that had not been condensed (CG) were sent to the medium-pressure absorber (MA). In the medium-pressure absorber the gases were absorbed in a low-pressure carbamate stream (LC) and condensed to form a carbamate stream (MC). The gases that had not been absorbed (MG) were sent to the low-pressure recovery section.

The flow from the USS, SG, and CS was a complete gravity flow. No pumps or ejectors were used to move the fluid or gases.

Both reactor (R) and stripper (S) were placed on ground level.

The height of the high-pressure synthesis section was 26 m from ground level.

The invention claimed is:

1. Process for the production of urea from ammonia and carbon dioxide in a urea plant containing a high-pressure synthesis section comprising at least one reactor section, a stripper and a condenser/reactor section
    wherein all the high-pressure equipment is placed so that the height of the high-pressure section is less than 35 m from ground level and wherein at least one of the reactor sections comprises an apparatus for the separate distribution of ammonia over the volume of the reactor section,
    wherein the flow of the synthesis solution from the reactor section to the stripper, the flow of the mixed gas stream from the stripper to the condenser and of the condensate from the condenser to the reactor section is a gravity flow.

2. Process according to claim 1, wherein the height of the high-pressure synthesis section is less than 30 m from ground level.

3. Process according to claim 1, wherein said apparatus for the separate distribution of ammonia is a sparger.

4. Process according to claim 1, wherein the stripper and the reactor section are located at ground level.

5. Process according to claim 1, wherein the reactor section comprising the apparatus for the separate distribution of ammonia is a submerged condenser.

6. Process according to claim 1, wherein the reactor section is a horizontally placed combination of a submerged condenser and a reactor section, wherein the apparatus for the separate distribution of ammonia is placed in the condensation section.

7. Process according to claim 5, wherein the submerged condenser is placed horizontally.

8. Process according to claim 6, wherein the apparatus for the separate distribution of ammonia is placed in the condensation section, and is extended into the reaction section.

9. Process according to claim 1, where at least parts of the reactor and stripping sections are made of a an austenitic-ferritic duplex steel with a chromium content of between 26 and 35 wt. % and a nickel content of between 3 and 10 wt %.

10. Process for the production of urea from ammonia and carbon dioxide in a urea plant containing a high-pressure synthesis section comprising at least one reactor section, a stripper and a condenser
    wherein all the high-pressure equipment is placed so that the height of the high-pressure section is less than 35 m from ground level and wherein at least one of the reactor sections comprises an apparatus for the separate distribution of ammonia over the volume of the reactor section,
    wherein the reactor section is a horizontally placed combination of a submerged condenser and a reactor section, wherein the apparatus for the separate distribution of ammonia is placed in the condensation section.

11. Process according to claim 10, wherein the apparatus for the separate distribution of ammonia is placed in the condensation section, and is extended into the reaction section.

12. Process according to claim 10, wherein the height of the high-pressure synthesis section is less than 30 m from ground level.

13. Process according to claim 10, wherein said apparatus for the separate distribution of ammonia is a sparger.

14. Process according to claim 10, wherein the flow of the synthesis solution from the reactor section to the stripper, the flow of the mixed gas stream from the stripper to the condenser and of the condensate from the condenser to the reactor section is a gravity flow.

15. Process according to claim 10, wherein the stripper and the reactor section are located at ground level.

16. Process according to claim 10, wherein the reactor section comprising the apparatus for the separate distribution of ammonia is a submerged condenser.

17. Process according to claim 16, wherein the submerged condenser is placed horizontally.

18. Process according to claim 10, where at least parts of the reactor and stripping sections are made of a an austenitic-ferritic duplex steel with a chromium content of between 26 and 35 wt. % and a nickel content of between 3 and 10 wt %.

* * * * *